US008488930B2

(12) United States Patent
Papac et al.

(10) Patent No.: US 8,488,930 B2
(45) Date of Patent: Jul. 16, 2013

(54) WAVELENGTH CONVERTING ILLUMINATION PROBE (75) Inventors: Michael James Papac, Tustin, CA (US);
Ronald T. Smith, Irvine, CA (US);
Michael J. Yadlowsky, Irvine, CA (US);
Michael McCulloch Martin, Newport Beach, CA (US); Christopher Horvath, Lake Forest, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 365 days.

(21) Appl. No.: 12/963,733

(22) Filed: Dec. 9, 2010

(65) Prior Publication Data

US 2012/0147329 A1 Jun. 14, 2012

(51) Int. Cl.
*G02B 6/06* (2006.01)

(52) U.S. Cl.
USPC .......................................................... 385/116

(58) Field of Classification Search
None
See application file for complete search history.

(56) References Cited

U.S. PATENT DOCUMENTS

| | | | |
|---|---|---|---|
| 4,227,939 A | | 10/1980 | Zewail et al. |
| 4,695,697 A * | | 9/1987 | Kosa ........................ 219/121.83 |
| 6,510,995 B2 | | 1/2003 | Muthu et al. |
| 6,540,670 B1 | | 4/2003 | Hirata et al. |
| 6,845,193 B2 * | | 1/2005 | Loeb et al. ...................... 385/33 |
| 6,850,673 B2 | | 2/2005 | Johnston, II et al. |
| 7,113,675 B2 * | | 9/2006 | Nield et al. ...................... 385/38 |
| 7,422,356 B2 * | | 9/2008 | Hama et al. .................. 362/574 |
| 7,758,224 B2 * | | 7/2010 | Hama et al. .................. 362/555 |
| 8,197,111 B2 * | | 6/2012 | Hama et al. .................. 362/555 |
| 2005/0251119 A1 | | 11/2005 | Eaton et al. |

FOREIGN PATENT DOCUMENTS

| | | |
|---|---|---|
| EP | 1522290 | 4/2005 |
| EP | 1734302 | 12/2006 |
| EP | 1867272 | 12/2007 |
| WO | WO 91/15793 | 10/1991 |
| WO | WO 2008/106590 | 9/2008 |

OTHER PUBLICATIONS

International Search Report for PCT/US2010/021001, Publication No. WO2010/085414, 5 pages.
Written Opinion of the International Searching Authority, International Application No. PCT/US2010/021001, 7 pages.
Fibertech Co., Ltd., "Product Information (Medical Endoscope)", 2008 FiberTech Co., Ltd., http://www.fibertech.jp/eng/m1.html.
Sumita Optical Glass, Inc., "Light Guides", 1996-2009 SUMITA Optical Glass, Inc., http://www.sumita-opt.co.jp/en/fiber.htm#2.

* cited by examiner

*Primary Examiner* — Sung Pak
(74) *Attorney, Agent, or Firm* — Keiko Ichiye (57) ABSTRACT Disclosed is an exemplary wavelength converting illumination probe having an illumination probe that can be selectively connected to a light source configured to generate light at a first wavelength range. The illumination probe including a lumen defining an aperture in a distal end of the illumination probe for emitting light. The wavelength converting illumination probe further including a wavelength converting element disposed within the lumen of the illumination probe. The wavelength converting element operable for receiving light from the light source at the first wavelength range, and converting the light to a second wavelength range.

17 Claims, 6 Drawing Sheets

WAVELENGTH CONVERTING ILLUMINATION PROBE

BACKGROUND

Anatomically, an eye may be divided into two distinct parts—an anterior segment and a posterior segment. The anterior segment includes a lens and extends from an outermost layer of the cornea (the corneal endothelium) to a posterior of a lens capsule. The posterior segment includes a portion of the eye behind the lens capsule. The posterior segment extends from an anterior hyaloid face (part of a vitreous body) to a retina, with which the posterior hyaloid face is in direct contact. The posterior segment is much larger than the anterior segment.

The posterior segment includes the vitreous body—a clear, colorless, gel-like substance. It makes up approximately two-thirds of the eye's volume, giving it form and shape before birth. The vitreous body is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free flowing like the aqueous humor and has normal anatomic attachment sites. One of these sites is the vitreous base, which is an approximately 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to the aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions, such as a fiber optic light source, to illuminate inside the eye; an infusion line to maintain the eye's shape during surgery; and instruments to cut and remove the vitreous body.

During such surgical procedures, proper illumination of the inside of the eye is important. Typically, a thin optical fiber is inserted into the eye to provide the illumination. A light source, such as a halogen tungsten lamp or high pressure arc lamp (metal-halides, Xe), may be used to produce the light carried by the optical fiber into the eye. The light passes through several optical elements (typically lenses, mirrors, and attenuators) and is transmitted to the optical fiber that carries the light into the eye. The advantage of arc lamps is a small emitting area (<1 mm), a color temperature close to daylight, and typically a longer life than halogen lamps (i.e., 400 hours vs. 50 hours). The disadvantage of arc lamps is high cost, decline in power, complexity of the systems and the need to exchange lamps several times over the life of the system.

In an effort to overcome some of the limitations of halogen tungsten lamps and high pressure arc lamps, other light sources, such as light emitting diodes (LEDs), may be used to produce the light transmitted through the optical fiber into the eye. LED based illuminators may be provided at considerably lower cost and complexity, and may exhibit characteristic life times of 50,000 to 100,000 hours, which may enable operating an ophthalmic fiber illuminator for the entire life of the instrument with very little drop in output and without the need to replace LEDs. LED light sources, however, generally exhibit lower luminous efficiency and decreased luminous flux than comparable halogen tungsten lamps and high pressure arc lamps.

DETAILED DESCRIPTION

Referring now to the discussion that follows and the drawings, illustrative approaches to the disclosed systems and methods are described in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive, otherwise limit, or restrict the claims to the precise forms and configurations shown in the drawings and disclosed in the following detailed description.

Figure 1:
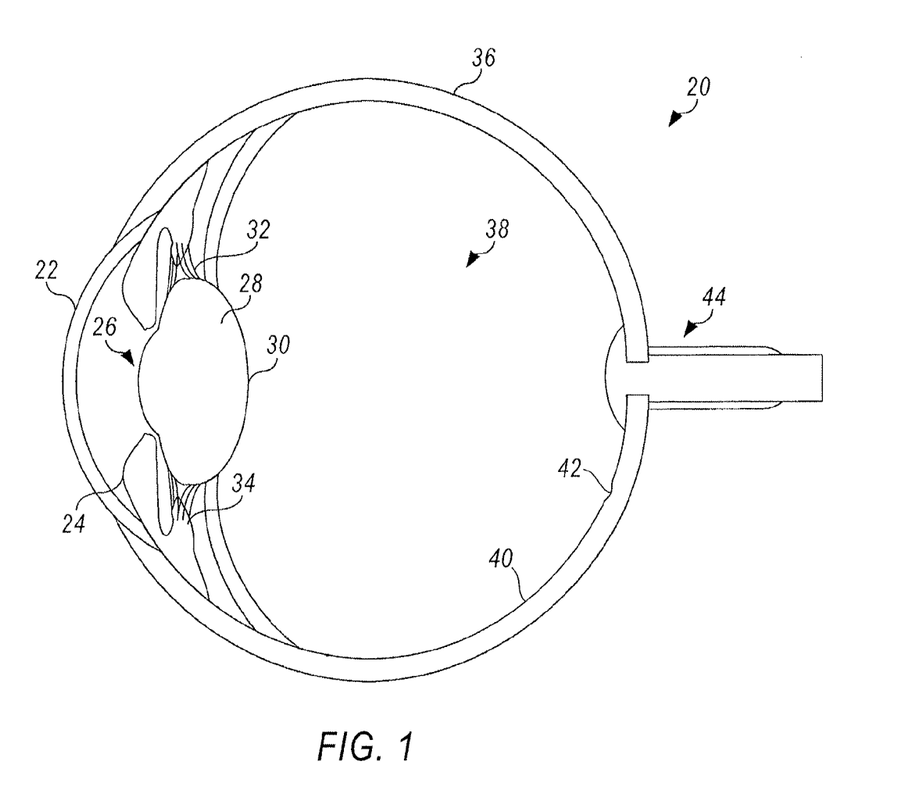
FIG. 1 is a cross-sectional view of an eye illustrating an internal anatomy of the eye.

FIG. 1 illustrates an anatomy of an eye 20, which includes a cornea 22, an iris 24, a pupil 26, a lens 28, a lens capsule 30, zonules 32, ciliary body 34, sclera 36, vitreous region 38, retina 40, macula 42, and optic nerve 44. Cornea 22 is a clear, dome shaped structure on the surface of eye 20 that acts as a window, letting light into the eye. Iris 24, which corresponds to the colored part of the eye, is a muscle surrounding pupil 26 that relaxes and contracts to control the amount of light entering eye 20. Pupil 26 is a round, central opening in iris 24. Lens 28 is a structure inside eye 20 that helps focus light on retina 40. Lens capsule 30 is an elastic bag that encapsulates lens 30, helping to control the shape of lens 28 as the eye focuses on objects at different distances. Zonules 32 are slender ligaments that attach lens capsule 30 to the inside of eye 20, holding lens 28 in place. Ciliary body 34 is a muscular area attached to lens 28 that contracts and relaxes to control the size of the lens for focusing. Sclera 36 is a tough, outermost layer of eye 20 that maintains the shape of the eye. Vitreous region 38 is a large, gel-filled section located towards a back of eye 20 that helps maintain the curvature of the eye. Retina 40 is a light-sensitive nerve layer at the back of eye 20 that receives light and converts it into signals to send to the brain. Macula 42 is an area in the back of eye 20 that includes receptors for detecting fine detail in a viewed image. Optic nerve 44 transmits signals from eye 20 to the brain.

Figure 2:
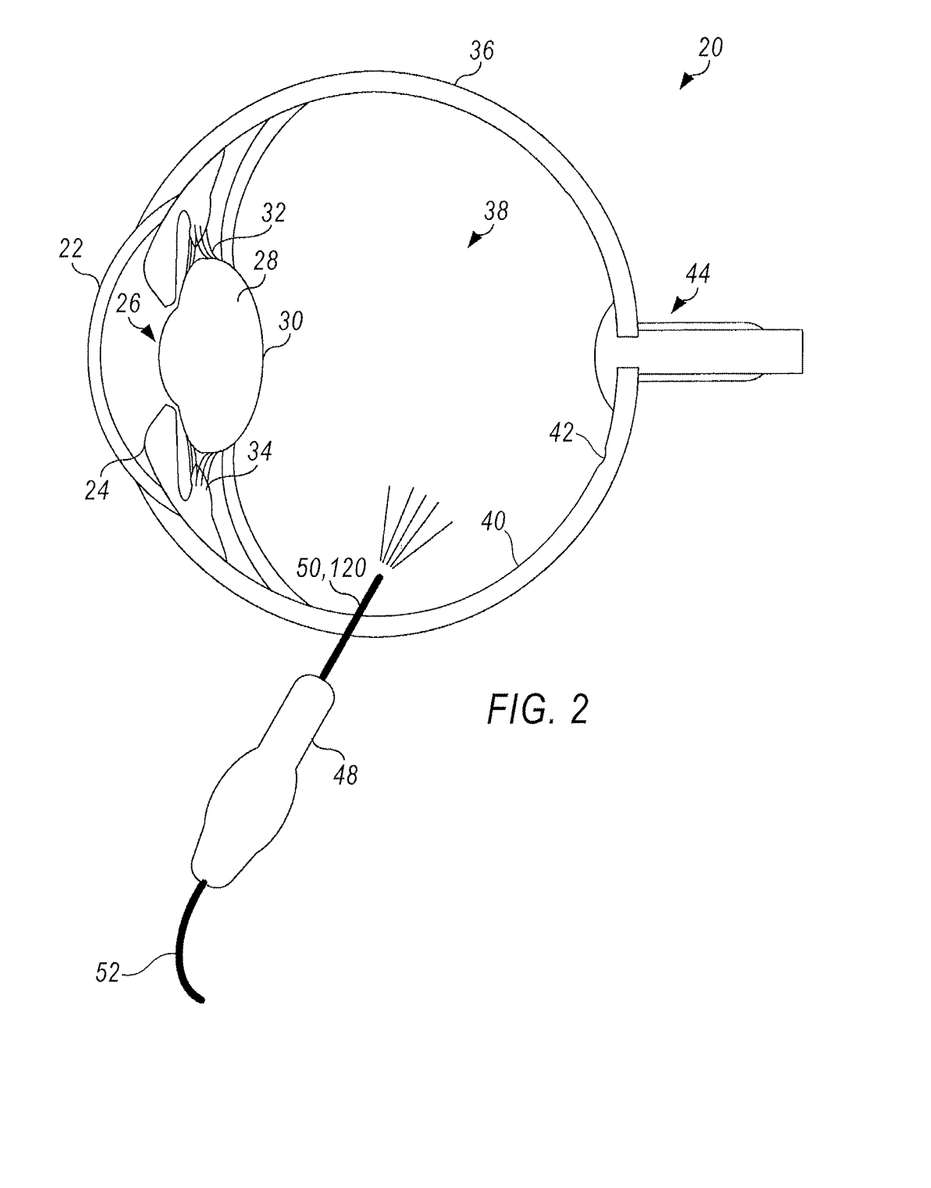
FIG. 2 is schematic illustration of exemplary illumination probe shown illuminating an interior region of the eye of FIG. 1.

With reference to FIG. 2, an illumination probe 50 for illuminating an interior of eye 20 is shown inserted through sclera 36 into vitreous region 38. Illumination probe 50 may include a handpiece 48 and a fiber optic cable 52 for transferring light from an illuminator to illuminate the inside of vitreous region 38 of eye 20 during various intra-optical procedures, such as vitreo-retinal surgery.

Figure 3:
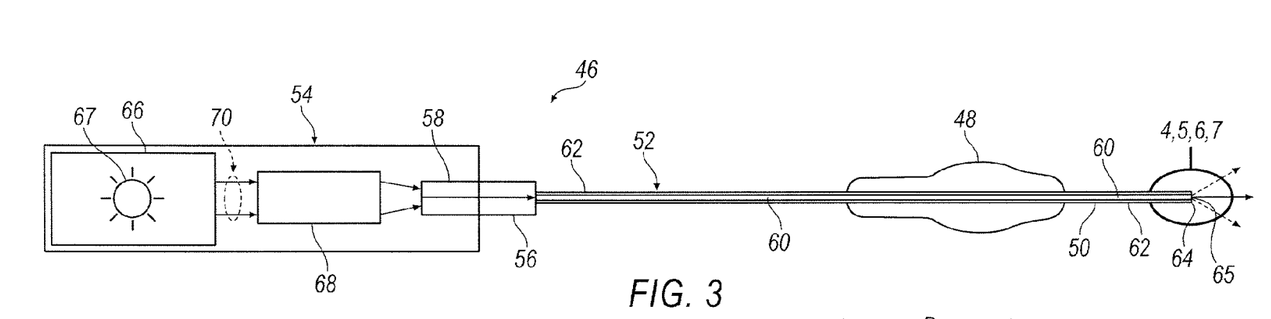
FIG. 3 is a schematic partial cross-sectional view of an exemplary endoilluminator employing an illumination probe that includes a wavelength converting element.

With reference to FIG. 3, an exemplary endoilluminator 46 may include an illuminator 54 for producing light that may be used to illuminate vitreous region 38 of eye 20. Light produced by illuminator 54 may be transmitted to the interior region of the eye through fiber optic cable 52. Fiber optic cable 52 may include a fiber optic connector 56 for optically connecting fiber optic cable 52 to illuminator 54. Fiber optic connector 56 releasably connects to a correspondingly configured illuminator optical connector 58 operably associated with illuminator 54. Optical connectors 56 and 58 enable fiber optic cable 52 to be selectively attached and detached from illuminator 54. In the exemplary configuration of endoilluminator 46 illustrated in FIG. 3, fiber optic cable 52 is shown directly connected to illuminator 54. In practice, various additional optical elements may be disposed in the optical path between illuminator 54 and fiber optic cable 52. For example, illuminator 54 may be housed within a surgical console. An optical connector, configured similar to optical connector 58, may be arranged in a readily accessible location on the surgical console to provide access for optically connecting fiber optic cable 52 to the connector. A series of optical elements, such as an optic fiber, may be employed to optically connect illuminator 54 to the optical connector arranged on the outside of the surgical console. Other optical elements may also be employed for optically connecting fiber optic cable 52 to illuminator 54.

Continuing to refer to FIG. 3, fiber optic cable 52 may have any of a variety of configurations. Fiber optic cable 52 may include a flexible configuration to allow generally unimpeded manipulation of illumination probe 50. In the exemplary configuration shown in FIG. 3, fiber optic cable 52 includes an optically transmissive fiber optic core 60 surrounded by a cladding material 62 having a low index of refraction relative to core 60. Fiber optic core 60 may be made of various materials, including but not limited to, glass and plastics. Fiber optic cable 52 may also include additional layers, depending on the requirements of a particular application. For example, fiber optic cable 52 may include a buffer material encasing cladding material 62, as well as an outer protective jacket for shielding the cable's interior components from damage.

Handpiece 48 may be attached to fiber optic cable 52. Extending from an end of handpiece 48 is illumination probe 50. Handpiece 48 may be suitably configured to provide a generally comfortable and reasonably secure handhold for grasping and manipulating illumination probe 50.

Illumination probe 50 may have the same general configuration as fiber optic cable 52. Illumination probe 50 may have either a flexible or generally rigid configuration to accommodate the operating and performance requirements of a particular application. A distal end 64 of illumination probe 50 may include an opening 65 for emitting light produced by illuminator 54.

Continuing to refer to FIG. 3, illuminator 54 may employ a light engine 66 for generating light at a particular luminous flux and chromaticity. Light engine 66 may employ various light sources 67, including, but not limited to, lamp based light sources, such as halogen tungsten lamps and high-pressure arc lamps (metal-halides and Xe). Light emitting diodes (LEDs) may also be employed as light source 67. LEDs may provide considerably lower cost and complexity than comparable halogen tungsten lamps and high-pressure arc lamps. LEDs may have characteristic life times of 50,000-100,000 hours, which would generally enable operating ophthalmic endoilluminator 46 for the life of the instrument with minimal drop in output and without a need for replacing LEDs.

LEDs typically emit light within a relatively narrow range of wavelengths, such as ultraviolet (UV), violet, or blue light, depending on the semiconductor diode material employed. For example, Indium Gallium Nitride (InGaN) generally produces a blue light having a wavelength ($\lambda$) of approximately 450 nm<$\lambda$<500 nm. The relatively narrow light band is generally not suitable for illumination. The emitted spectrum may be tailored by employing, for example, phosphor of different colors as a wavelength converting material to produce light across a desired spectrum. The number and type of phosphor materials employed may be varied to produce light within a desired wavelength range.

Light engine 66 may also employ lasers as light source 67. Various types and configurations of lasers may be employed, including but not limited to, gas lasers, dye lasers, metal-vapor lasers, solid state lasers, and semiconductor lasers. The light may be emitted over a relatively wide or narrow range of wavelengths depending on the type of laser employed. Lasers are generally capable of producing light having a relatively high degree of coherence, as compared to other light sources, such as LEDs and lamp based light sources. High coherence enables the emitted light to be focused to smaller spot sizes for more efficient transmission to fiber optic cables. The ability to focus the emitted light to small spot sizes may enable the use of smaller optic fibers, which may in turn limit the size of an incision required to insert illumination probe 50 into the eye.

Continuing to refer to FIG. 3, illuminator 54 may include an optical coupler 68 for capturing and focusing light 70 emitted from light engine 66, and focusing the light for delivery to fiber optic cable 52. Optical coupler 68 may include various optical elements, such as, for example, a collimating lens for receiving the generally divergent light beam 70 emitted from light engine 66, and a condensing lens arranged optically downstream of the collimating lens. The collimating lens receives light 70 emitted from light engine 66, and refracts the light to form a generally collimated light beam. The collimated light beam passes through the condensing lens, which operates to focus the collimated light beam for delivery to fiber optic cable 52. Optical coupler 68 may alternatively employ a ball lens for optically coupling light engine 66 to fiber optic cable 52. These are just two examples of the various optical coupling systems that may be employed to optically couple light engine 66 to fiber optic cable 52. Other optical coupling systems may also be utilized.

Light engine 66 may be configured to emit light within a selected wavelength range. It may be advantageous, however, to configure light engine 66 to emit light over a relatively narrow wavelength range. Emitting light within a narrow wavelength range may enable use of lower cost fiber optic components for fiber optic cable 52. Certain low cost fiber optics may be specifically tuned for efficient transmission of the relatively narrow bandwidth light emitted from light engine 66. Further, the wavelength converting system typically employed with certain narrowband light sources to produce generally broadband white light, such as phosphors and florescent materials employed with LEDs, generally produce an incoherent light that may difficult to focus to a small spot size. Generally, the larger the focal spot size the larger the fiber optic required to effectively capture and transmit the light. As is the case with many surgical procedures, including vitreo-retinal procedures, it is generally desirable to limit incisions to as small a size as possible. Smaller fiber optics generally require smaller incisions for insertion into the eye. Depending on the size of the fiber optic employed, the incision may be small enough to render the resulting wound substantially self-healing, thereby eliminating the need to employ additional procedures to close the incision, such as sutures. Configuring light engine 66 to produce narrow bandwidth light may also reduce the complexity and cost of the design, for example, by enabling the use of a single LED or laser as light source 67.

Figure 4:
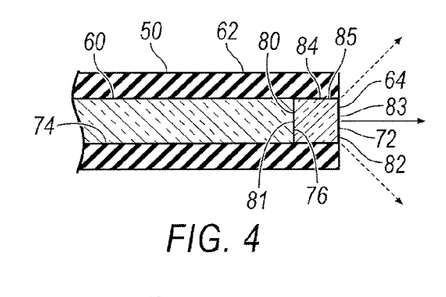
FIG. 4 is a schematic partial cross-sectional view of a distal end of the illumination probe of FIG. 3, with the wavelength converting element arranged adjacent the distal end of the illumination probe.
Figure 5:
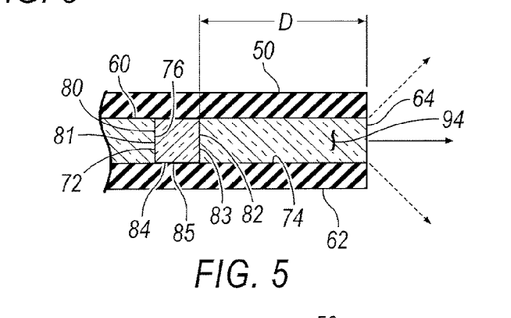
FIG. 5 is a schematic partial cross-sectional view of the distal end of the illumination probe of FIG. 3, with the wavelength converting element displaced inward from the distal end of the illumination probe.

Referring also to FIGS. 4 and 5, to take advantage of potential cost and optical transmission efficiencies that may be available when employing an LED or laser as light source 67, illumination probe 50 may include a wave length converting element 72 configured to convert the relatively narrow bandwidth light emitted from light source 67 to a generally broadband white light suitable for illuminating an interior region of eye 36 (FIG. 2). Wavelength converting element 72 may be arranged within a lumen 74 of illumination probe 50. Wavelength converting element 72 may be positioned immediately adjacent distal end 64 of illumination probe 50, as shown in FIG. 4, or disposed inward a distance D from distal end 64, as shown in FIG. 5. Wavelength converting element 72 may be arranged to abut an end 76 of fiber optic core 60, as shown in FIGS. 4 and 5, or may be displaced a distance from end 76. Further, additional optical elements may be disposed in the optical path between fiber optic core 60 and wavelength converting element 72, such as, for example, dichroic reflectors and filters for controlling the distribution of light emitted from the wavelength converting element.

Wavelength converting element 72 may have any of a variety of configurations. The term "wavelength converting element", as used herein, refers generally to any structure formed from a material capable of converting electromagnetic radiation, in a particular range of the electromagnetic spectrum, to another range within the electromagnetic spectrum, including but not limited to, the conversion of high-energy particle rays, x-rays and UV radiation to lower energy photons. Any suitable type of wavelength converting element for producing illumination may be employed. The luminescence process utilized for conversion may be based on either slow emission (phosphorescence) or fast emission (fluorescence), depending on the type of materials used in wavelength converting element 72.

For convenience, light having a wavelength within the range produced by light source 67 shall hereinafter be referred to as "unconverted light", whereas light having a wavelength within the range produced by wavelength converting element 72 shall hereinafter be referred to as "converted light". Furthermore, light having a wavelength within the range produced by light source 67 (i.e., unconverted light) is represented throughout the figures by a solid line, and light having a wavelength within the range produced by wavelength converting element 72 (i.e., converted light) is represented throughout the figures by a dashed line.

Wavelength converting element 72 may be used, for example, to convert UV/violet/blue light emitted from light source 67 into broadband or white light through luminescence or phosphorescence. The luminescence/phosphorence conversion process generally emits light in all directions, rather than along a particular light beam path. As a result, a portion of the converted light may be transmitted back through fiber optic core 60 toward illuminator 54. Further, not all of the unconverted light from light source 67 that reaches wavelength converting element 72 is converted to the desired wavelength range. Instead, a portion of the unconverted light may pass entirely through wavelength converting element 72. Both of these phenomena operate to reduce the operating efficiency of endoilluminator 46.

The conversion efficiency of wavelength converting element 72 may be maximized, for example, through application of one or more dichroic coatings to the surface of wavelength converting element 72. For example, a first dichroic coating 80 may be applied to an upstream face 81 of wavelength converting element 72. Dichroic coating 80 may be formulated to allow unconverted light from light source 67 to pass through the dichroic coating to wavelength converting element 72, and to reflect converted light towards distal end 64 of illuminator probe 50. Similarly, a second dichroic coating 82 may be applied to a downstream face 83 of wavelength converting element 72. Second dichroic coating 82 may be formulated to allow converted light to pass through second dichroic coating 82, and to reflect unconverted light back into wavelength converting element 72. Further, a reflective optical coating 84 may be applied to an outer circumference 85 of wavelength converting element 72 between first dichroic coating 80 and second dichroic coating 82. Reflective optical coating 84 may be configured as a broadband reflector to reflect both converted and unconverted light back into wavelength converting element 72. First and second dichroic coatings 80 and 82, and reflective optical coating 84, may together operate to help prevent unconverted light from escaping wavelength converting element 72, which may increase the efficiency of the conversion process.

Figure 6:
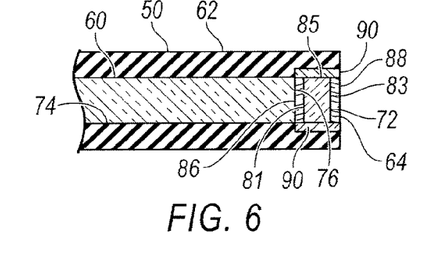
FIG. 6 is a schematic partial cross-sectional view of the distal end of the illumination probe of FIG. 4 configured to include optical elements for improving the conversion efficiency of the wavelength converting element.
Figure 7:
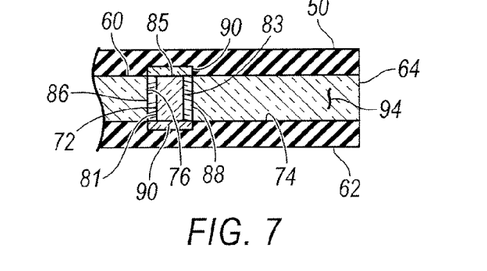
FIG. 7 is a schematic partial cross-sectional view of the distal end of the illumination probe of FIG. 5 configured to include optical elements for improving the conversion efficiency of the wavelength converting element.

With reference to FIGS. 6 and 7, first and second dichroic coatings 80 and 82, and reflective optical coating 84, may be configured as separate components, rather than as a coating applied to wavelength converting element 72. For example, a first dichroic element 86 having similar optical properties as first dichroic coating 80, may be arrange between end 76 of fiber optic core 60, and upstream face 81 of wavelength converting element 72. Similarly, a second dichroic element 88 having similar optical properties as second dichroic coating 82, may be arranged adjacent downstream face 83 of wavelength converting element 72. A reflective optical element 90 having similar reflective characteristics as reflective optical coating 84, may be arranged adjacent outer circumference 85 of wavelength converting element 72.

With reference to FIGS. 5 and 7, for configurations in which wavelength converting element 72 is displaced inward from end 64 of illumination probe 50, at least a portion of lumen 74 extending between end 64 of illumination probe 50 and wavelength converting element 72 may be filled with an optically transmissive material 94, or may alternately consist of a hollow cavity devoid of any material. Optically transmissive material 94 may be similarly configured and have similar optical properties as fiber optic core 60, or may be selectively configured to tailor the spectral properties of the light emitted from illumination probe 50.

Referring to FIGS. 4 and 5, light emitted from opening 65 of illumination probe 50 tends to diverge as the light travels away from the end of the illumination probe. The position of wavelength converting element 72 relative to end 64 of illumination probe 50 may affect the rate of divergence. As mentioned previously, the luminescence/phosphorescence conversion process employed within wavelength converting element 72 tends to emit light in all directions, rather than along a particular light beam path. By positioning wavelength converting element inward from end 64 of illumination probe 50, such as shown in FIGS. 5 and 7, the portion of lumen 74 located downstream of wavelength converting element 72 tends to collimate the light emitted from the wavelength converting element. Moving wavelength converting element 72 further away from end 64 of illumination probe 50 tends to increase the level of collimation, whereas moving wavelength converting element 72 toward end 64 of illumination probe 50 tends to decrease the level of collimation. There may be a limit to the level of collimation that may be achieved by moving wavelength converting element away from end 64 of illumination probe 50, which may correspond to the level of collimation naturally occurring within fiber optic cable 52. The rate of divergence of light emitted from illumination probe 50 may be maximized by arranging wavelength converting element 72 at least flush with end 64 of illumination probe 50, such as shown FIG. 4, or by positioning the wavelength converting element to partially extend beyond end 64 of illumination probe 50. Conversely, the level of divergence may be minimized by positioning wavelength converting element 72 at a distance from end 64 of illumination probe 50, such that that the convergence level of the emitted light approaches the convergence level of fiber optic cable 52.

In the exemplary configuration of illumination probe 50 shown in FIGS. 4-7, wavelength converting element 72 is configured to have substantially the same diameter as lumen 74. In practice, however, wavelength converting element 72 may have a larger or smaller diameter than lumen 74. Further, the portion of lumen 74 arranged upstream of wavelength converting element 72 (i.e., between wavelength converting element 72 and illuminator 54) and the portion of lumen 74 extending between wavelength converting element 72 and end 64 of illumination probe 50, may have different diameters, either or both of which may be larger or smaller than the diameter of wavelength converting element 72.

Figure 8:
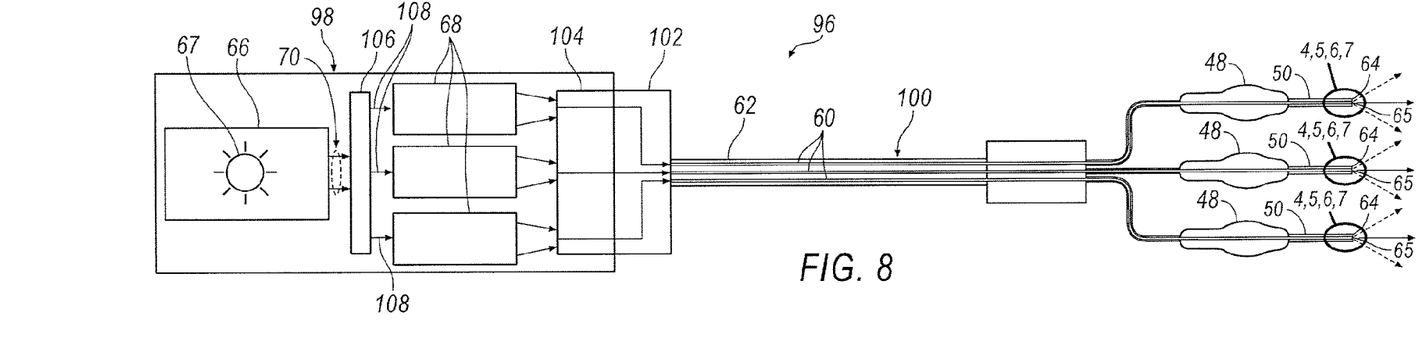
FIG. 8 is a schematic partial cross-sectional view of an exemplary endoilluminator employing multiple illumination probes, each probe including a wavelength converting element.

With reference to FIG. 8, an endoilluminator 96 may be configured for delivering light from an illuminator 98 to multiple illumination probes 50. Three illumination probes 50 are employed in the exemplary configuration of endoilluminator 96 illustrated in FIG. 8, but in practice, fewer or more probes 50 may also be employed. Illuminator 98 may include light engine 66 for generating light for illuminating the vitreous region 38 of eye 20 (FIG. 2). Light engine 66 may be similarly configured as previously described, and may include light source 67 for generating the illumination. Light source 67 may employ various light sources, including but not limited to, lamp based light sources, such as halogen tungsten lamps and high-pressure arc lamps (metal-halides and Xe), light emitting diodes (LEDs), and lasers.

Illuminator 98 may include a beam splitter 106 for splitting light beam 70 emitted from light engine 66 into multiple light beams 108 for delivery to the individual illumination probes 50. Beam splitter 106 may have any of a variety of configurations. Beam splitter 106 is represented schematically in FIG. 8 as a single rectangle, but in practice may include a system of multiple beam splitters configured to split light beam 70 emitted from light engine 66 into a selected number of individual beams. In the exemplary configuration of endoilluminator 96 illustrated in FIG. 8, beam splitter 106 may be configured to emit the three separate light beams 108. Each of the light beams 108 may have similar spectral properties. Beam splitter 106 may be configured to produce a different number of light beams than illustrated in FIG. 8, for example, to correspond to the number of illumination probes 50 employed.

Each individual light beam 108 emitted from beam splitter 106 may pass through a corresponding optical coupler 68 for capturing and focusing the individual light beams 108 for delivery to the individual illumination probes 50. As described previously, optical couplers 68 may include various optical elements focusing the light beam emitted from beam splitter 106.

Light produced by illuminator 98 may be transmitted to illumination probes 50 through a fiber optic cable bundle 100. Fiber optic cable bundle 100 may include a fiber optic connector 102 for optically connecting fiber optic cable bundle 100 to illuminator 98. Fiber optic connector 102 releaseably connects to a correspondingly configured illuminator optical connector 104 associated with illuminator 98. Optical connectors 102 and 104 enable fiber optic cable bundle 100 to be selectively attached and detached from illuminator 98. In the exemplary configuration of endoilluminator 98 illustrated in FIG. 8, fiber optic cable bundle 100 is shown directly connected to illuminator 98. However, in practice, various additional optical elements may be disposed in the optical path between illuminator 98 and fiber optic cable bundle 100, such as those described with respect to endoilluminator 46.

Continuing to refer to FIG. 8, fiber optic cable bundle 100 may be similarly configured as fiber optic cable 52 of endoilluminator 46 (FIG. 3). A difference being that fiber optic cable bundle 100 includes multiple fiber optic cores 60 for delivering illumination to the multiple illumination probes 50, rather than the single fiber optic core 60 employed with fiber optic cable 52. A separate fiber optic core 60 may be provided for each illumination probe 50 employed.

Fiber optic cable bundle 100 may include a flexible configuration to allow generally unimpeded manipulation of illumination probes 50. The multiple fiber optic cores 60 included in fiber optic cable bundle 100 may be surrounded by cladding material 62 having a low index of refraction relative to core 60. Fiber optic cores 60 may be made of various materials, including but not limited to, glass and plastics. Fiber optic cable bundle 100 may also include additional layers to accommodate various design requirements of a particular application. For example, fiber optic cable bundle may include a buffer material encasing cladding material 62, as well as an outer protective jacket for shielding the cable's interior components from damage.

Continuing to refer to FIG. 8, each illumination probe 50 may include a separate handpiece 48. Handpieces 48 may be suitably configured to provide a generally comfortable and reasonably secure handhold for grasping and manipulating illumination probe 50 associated with the respective handpiece 48. Each illumination probe 50 may have either a flexible or generally rigid configuration in order to accommodate the operating and performance requirements of a particular application. A distal end 64 of illumination probe 50 may include an opening 65 for emitting light produced by illuminator 98.

Referring to FIGS. 4-8, each illumination probe 50 of endoilluminator 96 (FIG. 8) may include a separate wavelength converting element 72 disposed within lumen 74 of illumination probe 50, such as shown, for example, in FIGS. 4-7. Wavelength converting element 72 may be positioned immediately adjacent distal end 64 of illumination probe 50, as shown in FIG. 4, or disposed inward a distance D from distal end 64, as shown in FIG. 5. Wavelength converting element 72 may be arranged to abut an end 76 of fiber optic core 60, as shown in FIGS. 4 and 5, or may be displaced a distance D from end 76.

Each wavelength converting element 72 employed with endoilluminator 96 may be configured substantially as previously described and illustrated in FIGS. 4-7. Wavelength converting elements 72 receive the generally narrow bandwidth light emitted from light engine 66, and convert at least a portion of the light to a selected range of the electromagnetic spectrum. Each wavelength converting element 72 may be configured to emit light within substantially the same spectral range, or different spectral ranges.

Continuing to refer to FIGS. 4-8, one or more dichroic and reflective coatings, such as dichroic coatings 80 and 82 and reflective optical coating 84 (FIGS. 4 and 5), may be employed with one or more of the wavelength converting elements 72 employed with endoilluminator 96 (FIG. 8) to help maximize the conversion efficiency. The dichroic and reflective coatings may be applied to wavelength converting element 72, such as shown in FIGS. 4 and 5 for example, or may be configured as separate components, such as first and second dichroic elements 86 and 88, and reflective optical element 90, as shown in FIGS. 6 and 7.

Figure 9:
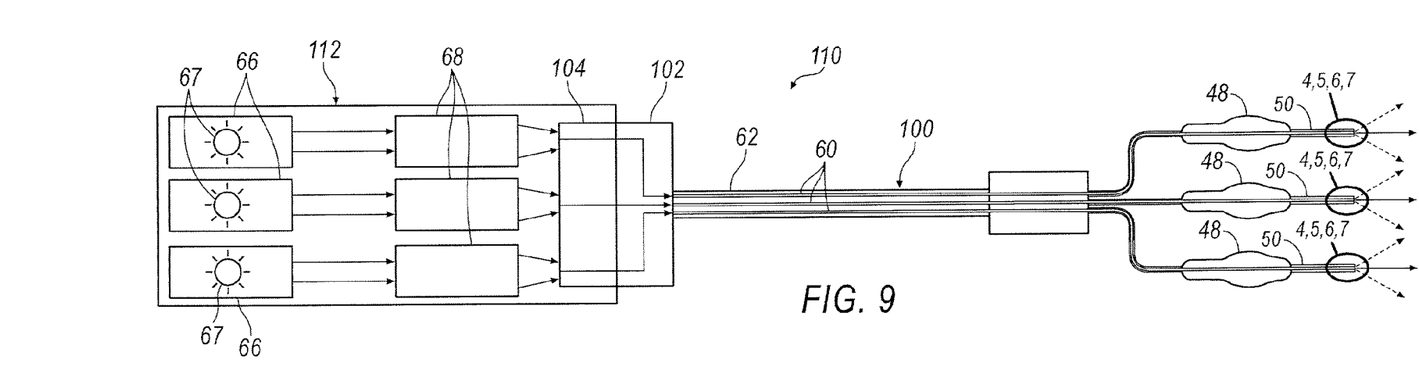
FIG. 9 is a schematic partial cross-sectional view of an exemplary endoilluminator employing multiple light engines for supplying light to multiple illumination probes, each probe including a wavelength converting element.

With reference to FIG. 9, an endoilluminator 110 may include an alternately configured illuminator 112 for generating light at a particular luminous flux and chromaticity. Illuminator 112 may be similarly configured as illuminator 98 (FIG. 8), but differs by including multiple light engines 66 for delivering light to multiple illumination probes 50. A separate light engine 66 may be provided for each of the available illumination probes 50. Three light engines 66 are shown in the exemplarily configured endoilluminator 110, as illustrated in FIG. 9, one for each of the three illumination probes 50. In practice, illuminator 112 may be configured to include fewer or more light engines 66 to correspond with the total number of illumination probes 50 employed. Providing a separate light engine 66 for each illumination probe 50 eliminates the need for beam splitter 106 (FIG. 8). Aside from including additional light engines 66, and eliminating beam splitter 106, endoilluminator 110 may have a substantially similar configuration as endoilluminator 96 (FIG. 8), including the configuration of fiber optic bundle 100 and probes 50.

Figure 10:
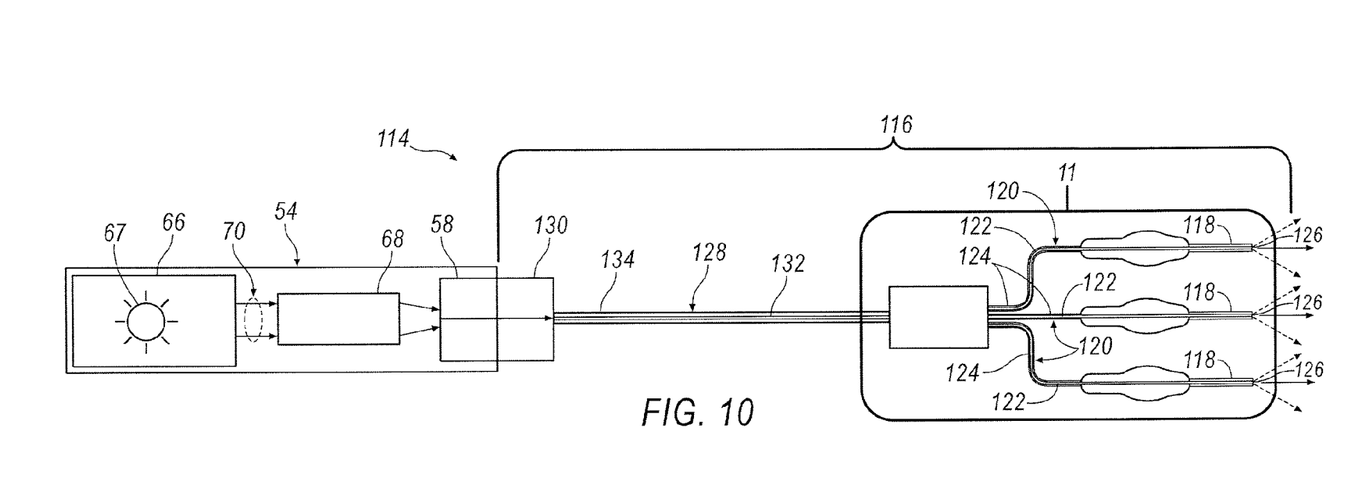
FIG. 10 is a schematic partial cross-sectional view of an exemplary endoilluminator employing a single light engine for supplying light to multiple illumination probes.

Referring to FIG. 10, an alternately configured endoilluminator 114 may include illuminator 54 for producing light for illuminating vitreous region 38 of eye 20. Illuminator 54 may be configured substantially as previously described in connection with endoilluminator 46, and may employ light engine 66 with light source 67 for generating light at a particular luminous flux and chromaticity. Illuminator 54 may include optical coupler 68 for capturing and focusing light 70 emitted from light engine 66 for delivery to a light delivery system, such as a fiber optic cable. Illuminator 54 may include illuminator optical connector 58 for optically connecting illuminator 54 to a fiber optic illumination delivery system 116 for transmitting light produced by illuminator 54 to interior region 38 of the eye 20 (FIG. 2).

Figure 11:
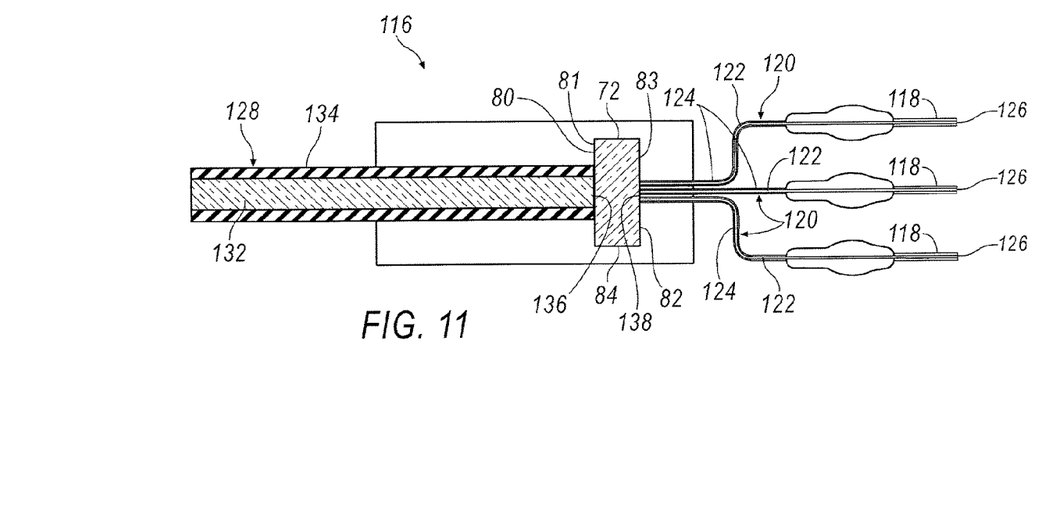
FIG. 11 is a schematic partial cross-sectional view of the illumination probes of FIG. 10, the endoilluminator including a single wavelength converting element.

Referring to FIGS. 10 and 11, illumination delivery system 116 may include multiple illumination probes 118, which may be similarly configured as illumination probe 50 employed in connection with endoilluminators 46 (FIG. 3), 96 (FIG. 8) and 110 (FIG. 10), but does not wavelength include a wavelength converting element 72 disposed within lumen 74 (FIGS. 4-7). Optically connected to each illumination probe 118 is a probe fiber optic cable 120, which may be similarly configured as fiber optic cable 52 employed with endoilluminators 46, 96 and 110. Probe fiber optic cable 120 may include a fiber optic core 122. Fiber optic core 122 may be made of various materials, including but not limited to, glass and plastics. Probe fiber optic cable 120 may include a cladding material 124 encasing fiber optic core 122. Cladding material 122 typically has a low index of refraction relative to fiber optic core 122. Fiber optic core 122 extends through illumination probe 118 to an end 126 of illumination probe 118. Light passing through fiber optic core 122 may be emitted from illumination probe 118 through an opening in end 126. Probe fiber optic cable 120 may include additional layers to accommodate the requirements of a particular application. For example, probe fiber optic cable 120 may include a buffer material encasing cladding material 124, as well as an outer protective jacket for shielding the cable's interior components from damage.

Light produced by illuminator 54 may be delivered to the multiple illumination probes 118 through a fiber optic cable 128, which may be similarly configured as fiber optic cable 52. A fiber optic connector 130 optically connects fiber optic cable 128 to illuminator 54. Fiber optic connector 130 releaseably connects to correspondingly configured illuminator optical connector 58 operably associated with illuminator 54. Fiber optic cable 128 may include an optically transmissive fiber optic core 132 surrounded by a cladding material 134 having a low index of refraction relative to fiber optic core 132. Fiber optic core 132 may be made of various materials, including but not limited to, glass and plastics. Fiber optic cable 128 may also include additional layers to accommodate the performance and operating requirements of a particular application. For example, fiber optic cable 128 may include a buffer material encasing cladding material 134, as well as an outer protective jacket for shielding the cable's interior components from damage.

Illumination delivery system 116 of endoilluminator 114 may include a wavelength converting element 72 positioned within an optical path between fiber optic cable 128 and the multiple probe fiber optic cables 120. In the exemplary configuration illustrated in FIGS. 10 and 11, wave length converting element 72 optically connects fiber optic cable 128 to probe fiber optic cables 120. An end 136 of fiber optic core 132 may be arranged adjacent upstream face 81 of wavelength converting element 72, and ends 138 of probe fiber optic cores 122 may be arranged adjacent downstream face 83 of wavelength converting element 72. In the exemplary configuration illustrated in FIG. 11, end 136 of fiber optic core 132, and ends 138 of probe fiber optic cores 122 are shown contacting wavelength converting element 72, but in practice, the ends of the fiber optic cores may be displaced away from the wavelength converting element. Further, additional optical elements may be disposed in the optical path between ends 138 and 136 of fiber optic cores 122 and 132, respectively, and wavelength converting element 72.

Continuing to refer to FIG. 11, wavelength converting element 72 may be configured as previously described in connection with endoilluminators 46, 96 and 110, and illustrated in FIGS. 4-7. For example, wavelength converting element 72 may be configured to convert the generally narrow band light received from illuminator 54 to a selected range of the electromagnetic spectrum. One or more dichroic and reflective coatings, such as dichroic coatings 80 and 82, and reflective optical coating 84, may be employed to help maximize the conversion efficiency of wavelength converting element 72. The dichroic and reflective coatings may be applied to wavelength converting element 72, or may be configured as separate components, such as first and second dichroic elements 86 and 88, and reflective optical element 90, for example, as shown in FIGS. 6 and 7.

Figure 12:
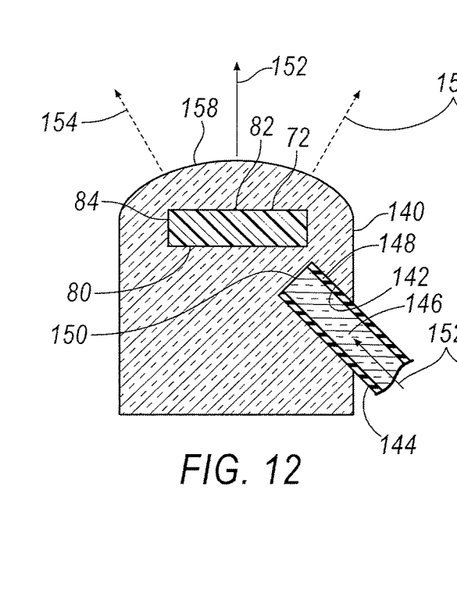
FIG. 12 is a schematic partial cross-sectional view of an encapsulated wavelength converting element including a port for receiving a fiber optic cable.
Figure 13:
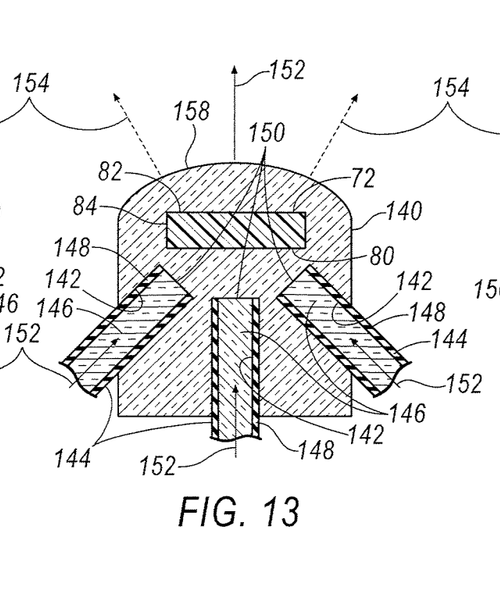
FIG. 13 is a schematic partial cross-sectional view of an encapsulated wavelength converting element including multiple ports for receiving multiple fiber optic cables.
Figure 14:
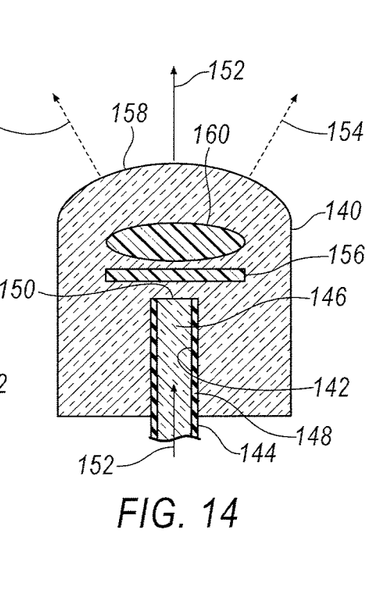
FIG. 14 is a schematic partial cross-sectional view on an encapsulated wavelength converting element employing a dichroic optical element.

With reference to FIGS. 12-14, wavelength converting element 72 may be may be encapsulated in an optically transmissive capsule 140. Capsule 140 may be made from various materials, including but not limited to, glass and plastic, so as to provide a generally impermeable barrier to bodily fluids and enhanced biocompatibility. Capsule 140 may include one or more ports 142 for optically connecting one or more fiber optic cable 144 to the capsule. Fiber optic cable 144 may be similarly configured as fiber optic cable 52 employed in connection with endoilluminators 46, 96 and 110. Fiber optic cable 144 may be optically connected to an illuminator, such as, for example, illuminators 54 (FIG. 3), 98 (FIG. 8), and 112 (FIG. 112), for transmitting the generally narrow band light emitted from the illuminator to capsule 140. Fiber optic cable 144 may be similarly configured as fiber optic cable 52 (FIG. 3), and may include a fiber optic core 146 encased in a cladding material 148. Cladding material 148 typically has a low index of refraction relative to fiber optic core 146. Light passing through fiber optic core 146 may be emitted from an end 150 into capsule 140. Fiber optic cable 144 may also include additional layers to accommodate the design requirement of a particular application. For example, fiber optic cable 144 may include a buffer material encasing cladding material 148, as well as an outer protective jacket for shielding the cable's interior components from damage.

Wavelength converting element 72 may be configured as previously described in connection with endoilluminators 46 (FIG. 3), 96 (FIG. 8), 110 (FIG. 9) and 114 (FIG. 10), and illustrated in FIGS. 4-7. Wavelength converting element 72 may be configured to convert light delivered to capsule 140 through fiber optic cable 144 to a selected range of the electromagnetic spectrum. For example, unconverted light 152 may pass through wavelength converting element 72, where at least a portion of the relatively narrow bandwidth light is converted to a generally broadband white light 154 (i.e., converted light) suitable for illuminating an interior region 38 of eye 36 (FIG. 2), or to another selected wavelength range. Not all of unconverted light 152 passing through wavelength converting element 72 may be converted to the selected wavelength range. A portion of unconverted light 152 may instead pass through wavelength converting element 72 and be emitted from capsule 140 as unconverted light 152, along with converted light 154.

One or more dichroic and reflective coatings, such as dichroic coatings 80 and 82 and reflective optical coating 84, such as shown in FIGS. 4 and 5, may be employed to help maximize the conversion efficiency of wavelength converting element 72. The dichroic and reflective coatings may be applied to wavelength converting element 72, or may be configured as separate components, such as first and second dichroic elements 86 and 88, and reflective optical element 90, for example, as shown in FIGS. 6 and 7. When employed as separate components, the dichroic elements may be disposed adjacent wavelength converting element 72, as shown in FIGS. 6 and 7, or displaced away from the wavelength converting element, such as, for example, dichroic element 156, as shown in FIG. 14. Dichroic element 156 may be configured, for example, to allow unconverted light 152 to pass through dichroic element 156, while reflecting converted light 154 emitted from wavelength converting element 72.

With continued reference to FIGS. 12-14, capsule 140 may include an optically shaped outer surface 158 through which both converted light 154 and unconverted light 152 may be emitted. Optical surface 158 may be contoured to selectively tailor the shape and focus of the emitted light beam.

Wavelength converting element 72 is depicted schematically throughout the drawing figures as having a generally rectangular shape. Other shapes may also be employed. An example of an alternatively shaped wavelength converting element 160 is illustrated in FIG. 14. The wavelength converting element may also have any of a variety of other shapes and sizes to accommodate the performance and design requirements of a particular application.

It will be appreciated that the exemplary wavelength converting illumination probe described herein has broad applications. The foregoing configuration were chosen and described in order to illustrate principles of the methods and apparatuses as well as some practical applications. The preceding description enables others skilled in the art to utilize methods and apparatuses in various configurations and with various modifications as are suited to the particular use contemplated. In accordance with the provisions of the patent statutes, the principles and modes of operation of the disclosed wavelength converting illumination probe have been explained and illustrated in exemplary configurations.

It is intended that the scope of the present methods and apparatuses be defined by the following claims. However, it must be understood that the disclosed wavelength converting illumination probe may be practiced otherwise than is specifically explained and illustrated without departing from its spirit or scope. It should be understood by those skilled in the art that various alternatives to the configuration described herein may be employed in practicing the claims without departing from the spirit and scope as defined in the following claims. The scope of the disclosed wavelength converting illumination probe should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said,"

etc. should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. A wavelength converting illumination probe comprising:
   an illumination probe selectively connectable to a light source configured to generate light at a first wavelength range, the illumination probe including a lumen defining an aperture in a distal end of the illumination probe for emitting light;
   a wavelength converting element disposed within the lumen of the illumination probe, the wavelength converting element operable for receiving light from the light source at the first wavelength range, and converting the light to a second wavelength range;
   a first dichroic element disposed within the lumen and adjacent to the wavelength converting element, the first dichroic element configured to substantially allow passage of the converted light and to reflect the unconverted light back to the wavelength converting element; and
   an optically transmissive material disposed within the lumen at the distal end of the illumination probe and adjacent to the first dichroic element, the optically transmissive material configured to transmit the converted light from the first dichroic element, the first dichroic element disposed between the wavelength converting element and the optically transmissive material.

2. The wavelength converting illumination probe of claim 1 further comprising an optical cable for optically coupling the light source to the wavelength converting element.

3. The wavelength converting illumination probe of claim 2, wherein the optical cable includes a fiber optic core having an end disposed adjacent the wavelength converting element.

4. The wavelength converting illumination probe of claim 1, wherein at least a portion of the wavelength converting element is disposed within the aperture in the distal end of the illumination probe.

5. The wavelength converting illumination probe of claim 1, wherein the entire wavelength converting element is displaced away from the aperture in the distal end of the illumination probe.

6. The wavelength converting illumination probe of claim 1 further comprising:
   a second dichroic element disposed within the lumen and adjacent to the wavelength converting element, the second dichroic element configured to substantially allow passage of light at the first wavelength range and to reflect light at the second wavelength range towards the distal end.

7. The wavelength converting illumination probe of claim 1, wherein the light source includes at least one of a light emitting diode and a laser.

8. The wavelength converting illumination probe of claim 1 further comprising an optical reflector arranged adjacent the wavelength converting element, the optical reflector configure to reflect light across substantially the first and second wavelength ranges.

9. An illumination system comprising:
   a light source operable for generating light at a first wavelength range;
   an illumination probe including an aperture arranged in a distal end of the probe for emitting light;
   a fiber optic cable optically connected to the illumination probe and optically connectable to the light source, the fiber optic cable operable for transmitting light generated by the light source to the illumination probe, the fiber optic cable including an optical connector for selectively connecting the fiber optic cable to the light source;
   a wavelength converting element disposed in the optical path between the optical connector and the distal end of the illumination probe, the wavelength converting element operable for receiving light from the light source at the first wavelength range, and converting the light to a second wavelength range;
   a first dichroic element disposed within the lumen and adjacent to the wavelength converting element, the first dichroic element configured to substantially allow passage of the converted light and to reflect the unconverted light back to the wavelength converting element; and
   an optically transmissive material disposed within the lumen at the distal end of the illumination probe and adjacent to the first dichroic element, the optically transmissive material configured to transmit the converted light from the first dichroic element, the first dichroic element disposed between the wavelength converting element and the optically transmissive material.

10. The illumination system of claim 9, wherein the illumination probe includes a lumen optically connected to the aperture in the distal end of the illumination probe and the fiber optic cable, the wavelength converting element disposed within the lumen of the illumination probe.

11. The illumination system of claim 10, wherein at least a portion of the wavelength converting element is disposed within the aperture in the distal end of the illumination probe.

12. The illumination system of claim 10, wherein substantially the entire wavelength converting element is displaced away from the aperture in the distal end of the illumination probe.

13. The illumination system of claim 9 further comprising:
   at least two illumination probes optically connectable to the light source, each illumination probe including a wavelength converting element disposed within the lumen of the illumination probe; and
   at least one optical splitter disposed in the optical path between the light source and the at least two illumination probes, the optical splitter operable for splitting the light emitted from the light source into separate light beams for delivery to each wavelength converting element disposed within the at least two illumination probes.

14. The illumination system of claim 9 further comprising at least two illumination probes optically connectable to the light source, the wavelength converting element disposed in an optical path between the optical connector and the at least two illumination probes.

15. The illumination system of claim 9 further comprising:
   a second dichroic element disposed within the lumen and adjacent to the wavelength converting element, the second dichroic element configured to substantially allow passage of light at the first wavelength range and to reflect light at the second wavelength range towards the distal end.

16. An encapsulated wavelength converting element comprising:
   an at least partially optically transparent capsule including at least one port for receiving a fiber optic cable configured to transmit light at a first wavelength range, the optically transparent capsule comprising optically transmissive material;

a dichroic element encapsulated within the optically transmissive material such that a portion of the optically transmissive material is disposed between the dichroic element and the fiber optic cable, the dichroic element configured to substantially allow passage of light at the first wavelength range and to reflect light at a second wavelength range; and a wavelength converting element encapsulated within the optically transmissive material such that a portion of the optically transmissive material is disposed between the wavelength converting element and the dichroic element, the wavelength converting element operable for receiving light at the first wavelength range, and converting the light to the second wavelength range.

17. The encapsulated wavelength converting element of claim 16, wherein the capsule includes an optically shaped outer surface through which light emitted from the wavelength converting element passes, the wavelength converting element disposed in an optical path between the at least one port and the optically shaped outer surface.

* * * * *